United States Patent [19]

Hussmann et al.

[11] Patent Number: 4,721,815

[45] Date of Patent: Jan. 26, 1988

[54] PREPARATION OF SUBSTITUTED BENZOPHENONES

[75] Inventors: Gregory P. Hussmann, Warrenville; Carl A. Udovich, Joliet, both of Ill.

[73] Assignee: Amoco Corporation, Chicago, Ill.

[21] Appl. No.: 944,516

[22] Filed: Dec. 22, 1986

[51] Int. Cl.⁴ .............................................. C07C 45/65
[52] U.S. Cl. .................................... 568/312; 568/356
[58] Field of Search ............... 568/319, 312, 354, 356; 585/234

[56] References Cited

U.S. PATENT DOCUMENTS

| | | | |
|---|---|---|---|
| 2,586,486 | 2/1952 | Schwartymann | 568/312 |
| 2,697,729 | 12/1954 | Ohlson et al. | 568/397 |
| 3,043,852 | 7/1962 | Mills | 568/354 |
| 3,288,853 | 11/1966 | Muench et al. | 568/319 |
| 3,409,690 | 11/1968 | Fishel | 585/434 |
| 3,856,820 | 12/1974 | Hayes | 585/434 |
| 4,104,317 | 8/1978 | Antos | 585/434 |
| 4,271,327 | 6/1981 | Ishikawa et al. | 585/434 |

*Primary Examiner*—James H. Reamer
*Attorney, Agent, or Firm*—Gunar J. Blumberg; William H. Magidson; Ralph C. Medhurst

[57] ABSTRACT

There is disclosed a process for the preparation of a benzophenone, which process comprises contacting a feed comprising a 3-cyclohexene carboxylic acid in the vapor phase and under suitable conditions with a ketonic decarboxylative coupling catalyst to convert said carboxylic acid into a bis (3-cyclohexene) ketone and contacting said bis (3-cyclohexene) ketone with a dehydrogenation catalyst to dehydrogenate said bis (3-cyclohexene) ketone to provide said benzophenone. Suitably, the coupling catalyst comprises an oxide of manganese. A Group VIII metal-containing catalyst is a typical dehydrogenation catalyst.

5 Claims, No Drawings

PREPARATION OF SUBSTITUTED BENZOPHENONES

CROSS-REFERENCE TO RELATED APPLICATIONS

This application is being filed concurrently in the U.S. Patent and Trademark Office with U.S. Ser. No. 944,517, which is directed to the preparation of dialkyl ketones by the ketonic decarboxylative coupling of aliphatic carboxylic acids in the presence of a catalyst comprising manganese dioxide on a support of catalytically active alumina.

In addition, this application is being filed concurrently in the U.S. Patent and Trademark Office with U.S. Ser. No. 944,514, which is directed to the preparation of a benzophenone by the ketonic decarboxylative coupling of an aromatic carboxylic acid in the presence of a catalyst which is capable of catalyzing the conversion of an aromatic carboxylic acid to a benzophenone to provide a yield of at least 10% benzophenone and which comprises at least one oxide that is an oxide of an element having an atomic number of at least 60. Suitable catalysts are neodymium trioxide and a mixture of thorium dioxide and magnesium oxide.

BACKGROUND OF THE INVENTION

1. Field of the Invention

The present invention relates to a method or process for preparing aromatic ketones by a ketonic decarboxylative coupling of 3-cyclohexene carboyxlic acids. More particularly, the present invention relates to a process for preparing substituted benzophenones by means of a gas-phase or vapor-phase coupling of substituted 3-cyclohexene carboxylic acids and dehydrogenation of the resulting bis (3-cyclohexene) ketones.

2. Description of the Prior Art

It has been shown that ketones can be formed by means of ketonic decarboxylation of carboxylic acids. For example, in an article in ZH. OBSHCH. KHIM., 30, 9, 2789 (1960), Rubinshtein et al., discussed the use of $ThO_2$, $CeO_2$, $CaCO_3$, $BaCO_3$, $ZnO_2$, and $CdO$ as active catalysts for ketonization and the vapor-phase catalytic ketonization of acetic acid over carbonates of alkaline earth metals (Ca, Ba, Sr, and Mg). In KINET. KATAL., 2, 2, 172 (1961), Yakerson et al., investigated the kinetics of the thermal decomposition of lithium, sodium, and barium acetate to ketone and used the data to specify the mechanism of the vapor-phase ketonization of acetic acid and its decomposition to methane. In KINET. KATAL, 2, 6, 907 (1961), Yakerson et al., discussed the kinetics of vapor-phase catalytic ketonization of acetic acid over $TiO_2$, $ZrO_2$, $SnO_2$, $CeO_2$, and $BeO$. In IZV. AKAD. NAUK SSSR, No. 1, 83 (1966), Yakerson et al., discussed the catalytic ketonization of acetic acid over a mixed binary catalyst system of $ZrO_2$-$Al_2O_3$. In ZH. PRIKL. KHIM., 50, 2126 (1977), Shmelev et al., reported that diethyl ketone could be prepared by the ketonization of propionic acid in the presence of a catalyst of manganese dioxide supported on silica gel.

Furthermore, in Japanese Published Patent Application Kokai No. Sho. 57 (1982)-197237, Matsuoka disclosed a method for preparing ketones from straight-chain or branched aliphatic carboxylic acids by employing a gas-phase contact reaction whereby an aliphatic carboxylic acid is contacted with a catalyst comprising zirconium oxide and, optionally, a support of alumina or silica gel. In this Japanese patent publication, he also listed conventionally-used catalysts for the synthesis of a molecule of ketone from two molecules of a carboxylic acid as being calcium oxide, barium oxide, lithium oxide, alumina, chromium oxide, manganese oxide, thorium oxide, gallium oxide, indium oxide, and oxides of rare earth elements and mentioned that such catalysts provide low conversions and selectivities.

In U.S. Pat. No. 4,014,889, Schreckenberg et al., disclosed the preparation of a ketone by means of the reaction of an aromatic or heterocyclic aldehyde in the presence of a cyanide ion with an unsaturated compound having the formula:f

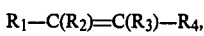

$$R_1-C(R_2)=C(R_3)-R_4,$$

wherein "$R_1$," "$R_2$," and "$R_3$" are the same or different and are selected from the group of hydrogen, optionally substituted aliphatic, cycloaliphatic, araliphatic, aromatic, heterocyclic and carboxylic ester and "$R_4$" is nitrile, $-CO-R_5$ or $-CO-OR_5$ wherein "$R_5$" is selected from the group of optionally substituted aliphatic, cycloaliphatic, araliphatic, aromatic, and heterocyclic and "$R_1$" and "$R_2$" and/or "$R_1$" and "$R_3$" and/or "$R_2$" and "$R_5$" or "$R_3$" and "$R_5$" together with the carbon atoms to which they are attached as substituents can also form a carbocyclic or heterocyclic ring.

In U.S. Pat. No. 3,479,400, Lese et al., disclosed a process for converting a 1,1-diarylalkane to the corresponding diaryl ketone, which process involves oxidizing the 1,1-diarylalkane in a first reaction zone with nitric acid, reacting the solid product from the first reaction zone with nitric acid in a second zone under conditions that are more severe than those employed in the first reaction zone to obtain the desired diaryl ketone and optionally recycling an aqueous solution containing nitric acid to the first reaction zone.

In U.S. Pat. No. 4,007,211, Trost et al., disclosed a method for converting an alpha-thiocarboxylic acid compound to the corresponding ketone. In this method, the carboxylic acid or its ester is first subjected to a sulfenylation reaction for positioning an "$-SR$" group alpha to the carboxylic acid group and then subjecting the sulfenylated product to oxidative decarboxylation.

It has now been found that aromatic ketones, such as benzophenones, can be prepared by the ketonic decarboxylative coupling of 3-cyclohexene carboxylic acids followed by the dehydrogenation of the intermediate product.

SUMMARY OF THE INVENTION

There is disclosed a process for preparing an aromatic ketone, such as a benzophenone, from a 3-cyclohexene carboxylic acid, which process comprises contacting a feed comprising said carboxylic acid in the vapor-phase and under suitable conditions with a ketonic decarboxylative coupling catalyst comprising an oxide of manganese to form a bis (3-cyclohexene) ketone and contacting said bis (3-cyclohexene) ketone with a dehydrogenation catalyst to provide said aromatic ketone (benzophenone). Suitable 3-cyclohexene carboxylic acids are 3-cyclohexene carboxylic acid, 4-methyl-3-cyclohexene carboxylic acid and 3,4-dimethyl-3-cyclohexene carboxylic acid.

Suitable dehydrogenation catalysts are Group VIII metals. Group VIII noble metals are preferred. Conveniently, the dehydrogenation catalyst can be supported on a catalytically active material, such as alumina. Alternatively, the dehydrogenation catalyst can be supported on the coupling catalyst.

DETAILED DESCRIPTION OF THE INVENTION

According to the present invention, there is provided a process for preparing an aromatic ketone by means of the ketonic decarboxylation of a carboxylic acid and the subsequent dehydrogenation of the resulting product. More particularly, there is provided a process for preparing a benzophenone by means of the ketonic decarboxylative coupling of 3-cyclohexene carboxylic acid and the subsequent dehydrogenation of the resulting bis (3-cyclohexene) ketone product. The coupling of 3-cyclohexene carboxylic acid provides improved yields of the desired aromatic ketone. A bis (3-cyclohexene) ketone is formed in high yield and can readily be dehydrogenated to the desired benzophenone.

Typical feeds for the process of the present invention are those containing 3-cyclohexene carboxylic acid, 4-methyl-3-cyclohexene carboxylic acid, 3,4-dimethyl-3-cyclohexene carboxylic acid, and mixtures thereof. Hence, the feedstock for this process can be a feed containing one or more 3-cyclohexene carboxylic acids. The 3-cyclohexene carboxylic acids can be prepared readily in excellent yields by the Diels-Alder reaction. For example, butadiene and acrylic acid can be heated under reflux in the presence of a benzene solvent and a Lewis acid catalyst, such as aluminum chloride, at a temperature of about 80° C. to form 3-cyclohexene carboxylic acid. In another example, 3,4-dimethyl-butadiene and acrylic acid can be employed to prepare 3,4-dimethyl-3-cyclohexene carboxylic acid. The resulting 3-cyclohexene carboxylic acid can then be used as a feed for the present invention.

The feed containing the 3-cyclohexene carboxylic acid can be subjected to a ketonic decarboxylative coupling and dehydrogenation sequence to provide the benzophenone.

The proposed sequence of ketonic decarboxylative coupling and dehydrogenation is exemplified by the following two reaction schemes:

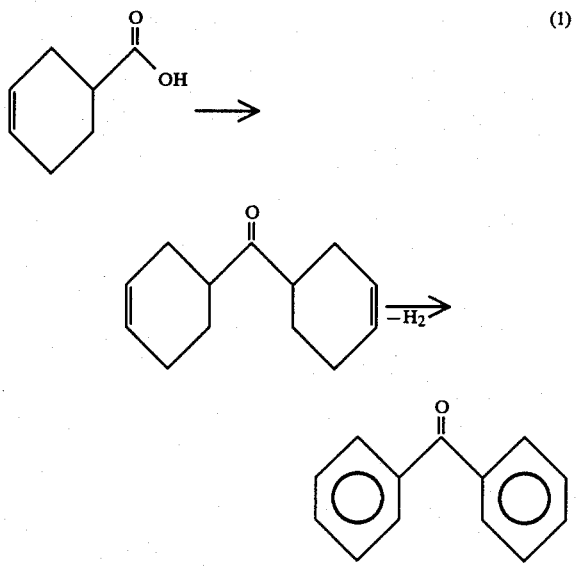

(1)

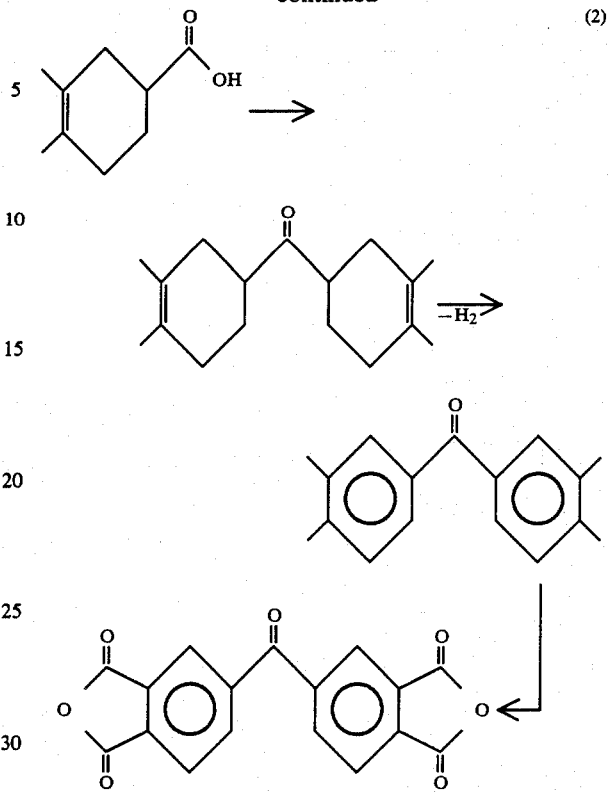

(2)

In one scheme, 3-cyclohexene carboxylic acid is converted to benzophenone; in the other, 3,4-dimethyl-3-cyclohexene carboxylic acid is converted to benzophenone dianhydride.

According to the present invention, there is provided a process for preparing a benzophenone from a 3-cyclohexene carboxylic acid, which process comprises contacting a feed comprising said carboxylic acid in the vapor phase and under suitable conditions with a ketonic carboxylative coupling catalyst comprising manganese dioxide to convert said carboxylic acid into a bis (3-cyclohexene) ketone and contacting said bis (3-cyclohexene) ketone in the vapor phase and under suitable conditions with a dehydrogenation catalyst to dehydrogenate said bis (3-cyclohexene) ketone to said benzophenone.

The ketonic decarboxylative coupling catalyst that is employed in the process of the present invention is a catalyst which comprises an oxide of manganese, namely, manganese dioxide. The manganese should have a valance of +4.

Optionally, the catalyst can also comprise a catalytically active alumina as a support material. Such alumina is readily accessible from catalyst manufacturers and catalyst vendors and should have a surface area within the range of about 5 m$^2$/gm to about 400 m$^2$/gm. Preferably, the surface area is in the range of about 50 m$^2$/gm to about 250 m$^2$/gm.

If the ketonic decarboxylative coupling catalyst is to be used without a support material, the catalytic material in the form of a powder can be compressed conveniently into tablets or pellets of desired size. For example, suitable pellets are those having a length of about 0.60 cm (0.24 in) and a diameter of about 0.015 cm (0.0063 in).

On the other hand, if the ketonic decarboxylative coupling catalyst is to have a support, the catalyst can be prepared conveniently by impregnating a support with a heat-decomposable solution of the metal being applied to the support material. Such impregnation can be performed by the incipient wetness technique, which involves employing just enough of the solution to fill the pores of the material that is being impregnated. The impregnated material is then calcined after drying. Drying can be carried out at a temperature within the range of about 100° C. to about 149° C., or higher, for a period of time within the range of about 1 hr to about 16 hr, while the calcination can be performed in air at a temperature within the range of about 454° C. to about 593° C., or higher, for a period of time within the range of about 0.5 hr to about 2 hr.

The finished supported catalyst contains manganese dioxide within the range of about 5 wt % to about 30 wt %, based upon the total weight of the catalyst. Preferably, the catalyst contains manganese dioxide within the range of about 10 wt % to about 25 wt %. A very effective ketonic decarboxylative coupling catalyst for use in the process of the present invention is a catalyst comprising about 19 wt % manganese dioxide on a support of alumina.

Any dehydrogenation catalyst, i.e., a catalyst comprising a hydrogenation-dehydrogenation metal, can be used in the process of the present invention. Preferably, a catalyst comprising a metal of Group VIII of the Periodic Table of Elements, such as nickel or cobalt, is employed. More preferably, a catalyst comprising a Group VIII noble metal is employed. The Group VIII noble metals, or platinum group metals are: platinum, palladium, osmium, ruthenium, rhodium, and iridium. Platinum and palladium are preferred platinum group metals.

Active dehydrogenation catalysts comprise the hydrogenation-dehydrogenation metal on a suitable catalytic support or carrier, such as a catalytically active alumina. Such catalyst can be prepared by impregnating the support with a heat-decomposable solution of the metal, as described hereinabove for the coupling catalysts. The completed catalyst can have a hydrogenation-dehydrogenation metal content within the range of about 0.1 wt % to about 10 wt %, based upon the total weight of the catalyst, preferably, within the range of about 0.5 wt % to about 5 wt %. In the case of a Group VIII noble metal, the catalyst will have a hydrogenation-dehydrogenation metal content within the range of about 0.1 wt % to about 2 wt %, based upon the total weight of the catalyst, preferably, within the range of about 0.5 wt % to about 1 wt %. Such hydrogenation-dehydrogenation catalyst can be purchased conveniently from catalyst manufacturers and suppliers.

Alternatively, the hydrogenation-dehydrogenation metal can be supported on the ketonic decarboxylative coupling catalyst. For example, the hydrogenation-dehydrogenation metal can be mixed with or impregnated on the coupling catalyst.

The catalyst system of the process of the present invention can comprise two distinct catalysts, a ketonic decarboxylative coupling catalyst and a dehydrogenation catalyst. The catalysts can be mixed together or the dehydrogenation catalyst can follow the coupling catalyst. On the other hand, a dual-functional catalyst, i.e., a catalyst that functions as both a ketonic decarboxylative coupling catalyst and a dehydrogenation catalyst, could conceivably be used. As shown hereinafter in Examples 11 and 12, a catalyst comprising manganese dioxide on an alumina support could be such a dual-functional catalyst.

The catalysts of the process of the present invention will become deactivated after a time because of an accumulation of coke (carbonaceous deposits). When deactivation does occur, the deactivated catalyst can be regenerated by means of heating it in air or an oxygen-containing gas at a temperature and for a period of time that are sufficient for burning off the coke.

According to the process of the present invention, the feed to be treated is contacted with the catalyst in a gas phase or vapor phase and under suitable conditions. Typical suitable conditions comprise a temperature within the range of about 250° C. to about 500° C., a pressure within the range of about 5 psia to about 200 psia, and a contact time within the range of about 1 sec to about 10 sec. Preferred conditions comprise a temperature within the range of about 325° C. to about 400° C., a pressure within the range of about 5 psia to about 35 psia, and a contact time within the range of about 3 sec to about 5 sec. Such conditions are suitable for both the ketonic decarboxylative coupling reaction and the dehydrogenation reaction.

One would expect the ketonic decarboxylative coupling of aromatic carboxylic acids to be an attractive way of preparing benzophenones. For example, 4,4'-dihydroxybenzophenone, a bis phenol A analog, and dianhydride might be prepared directly by coupling para-hydroxy benzoic acid and trimellitic anhydride respectively. Unfortunately, the utility of a direct coupling of aromatic carboxylic acids is limited by a competing undesirable decarboxylation reaction, which results in reduced selectivity and the formation of side products. It is of interest to note that aromatic carboxylic acids which contain strong electron donating groups, such as para-hydroxy benzoic acid, or strong electron withdrawing groups, such as para-nitro benzoic acid, do not yield appreciable quantities of an expected ketone coupling product. In general, such aromatic acids will undergo extensive decarboxylation. It is to be understood that aromatic acid ketonic decarboxylative coupling competes with the decarboxylation reaction and, consequently, low yields are often obtained. The process of the present invention provides benzophenones in improved yields, i.e., moderate to good yields. Consequently, the process provides an improved method for preparing benzophenones, the benzophenones being prepared from 3-cyclohexene carboxylic acids rather than from aromatic carboxylic acids.

While it is not intended to limit the scope of the process of the present invention by the following theory, it is postulated that gas-phase ketonic decarboxylative coupling occurs through the intermediacy of a metal carboxylate salt which decomposes in a carbanionic or radical fashion to the observed products.

The following examples are being presented to facilitate the understanding of the present invention. It is to be understood that these examples are presented for the purpose of illustration only and are not intended to limit the scope of the present invention.

All tests that were conducted in the following examples were performed in the gas-phase in a simple tube furnace reactor. Typically, a 5-ml portion of a 14/42-mesh catalyst material was charged into a quartz reactor, which was then placed in a single zone 12-inch Lindburg furnace controlled by a Eurotherm 919 system. The reactants were added at a rate of about 0.10 ml/min by means of a Harvard Apparatus syringe drive. Of course, solid reactants were necessarily dissolved in an inert solvent, such as toluene, prior to addition. Throughout the reaction, a 10 ml/min flow of nitrogen was swept through the reactor and the catalyst bed. The effluent from the reactor was collected in an ice-cooled receiving flask and analyzed by gas chromatography or liquid chromatography. Reaction products were identified by gas chromatography-mass spectroscopy or by comparison of retention time with that of an authentic sample. Quantitative analysis was performed by gas chromatography using internal standards and predetermined response factors.

The benzophenone materials produced by the process of the present invention are useful heat transfer agents and can be converted to useful monomers.

EXAMPLES 1-5

The coupling of 3-cyclohexene carboxylic acid was attempted in these examples. The catalyst employed and the temperatures are listed hereinbelow in Table I, along with the product distribution obtained in each test. The product distribution was calculated directly from percent gas chromatographic area. Cyclohexene and acrylic acid were formed in a reverse Diels-Alder reaction. The values for 3-cyclohexene carboxylic acid and bis (3-cyclohexene) ketone include isomers and analogous dehydrogenated products.

TABLE I

| | Coupling of 3-Cyclohexene Carboxylic Acid | | | | | |
|---|---|---|---|---|---|---|
| | | | | Product Distribution | | |
| Example | Catalyst | Temp. (°C.) | Cyclohexene | Acrylic Acid | 3-Cyclohexene Carboxylic Acid | Bis(3-Cyclohexene) Ketone |
| 1 | $ZrO_2$ | 365 | — | 15.7 | 71.5 | 2.6 |
| 2 | $ThO_2$ | 343 | — | 13.1 | 83.5 | — |
| 3 | $MnO_2$ | 343 | 2.3 | — | 60.5 | 12.0 |
| 4 | $MnO_2$ | 365 | 1.7 | — | 19.0 | 28.1 |
| 5 | 19% $MnO_2/Al_2O_3$ | 365 | 3.2 | — | 46.8 | 26.8 |

The results of the tests in these examples demonstrate that bis (3-cyclohexene) ketone can be obtained via ketonic decarboxylative coupling of 3-cyclohexene carboxylic acid. Moreover, the data demonstrate that a catalyst comprising manganese dioxide can provide yields of bis (3-cyclohexene) ketone in excess of 10%. The data also show that a catalyst comprising zirconium dioxide does furnish a small amount of the desired ketone.

EXAMPLES 6-10

The coupling of 3,4-dimethyl-3-cyclohexene carboxylic acid was attempted in each of these examples. The catalyst and temperatures that were employed, along with product distribution, are presented hereinbelow in Table II. Again the product distribution was calculated directly from percent gas chromatographic areas. The values include isomers and analogous dehydrogenated products.

TABLE II

| Coupling of 3,4-Dimethyl-3-Cyclohexene Carboxylic Acid | | | | |
|---|---|---|---|---|
| | | | Product Distribution | |
| Example | Catalyst | Temp. (°C.) | Carboxylic Acid | Ketone |
| 6 | $ThO_2$ | 343 | 80.6 | 3.6 |
| 7 | 98% $ZrO_2$, 2% $Al_2O_3$ | 343 | 82.3 | 2.0 |
| 8 | $MnO_2$ | 315 | 71.0 | 12.6 |
| 9 | $MnO_2$ | 370 | 24.3 | 60.1 |
| 10 | 19% $MnO_2/Al_2O_3$ | 357 | 20.0 | 64.4 |

Again a catalyst comprising manganese dioxide or manganese dioxide supported on alumina provided the best yields, i.e., yields in excess of 10%. Furthermore, the catalyst comprising thorium dioxide and the catalyst comprising zirconium dioxide did furnish some of the desired ketone. However, the yields were quite inferior to those provided by the catalysts comprising manganese dioxide.

EXAMPLES 11-12

A catalyst comprising 19 wt % $MnO_2$ on an alumina support, based upon the weight of the catalyst, was employed to convert 3-cyclohexene carboxylic acid and 3,4-dimethyl-3-cyclohexene carboxylic acid at a temperature of 360° C. and other conditions listed hereinabove. An approximate 53% conversion of 3-cyclohexene carboxylic acid and an approximate 80% conversion of 3,4-dimethyl-3-cyclohexene carboxylic acid were achieved. The ketone-containing coupling products were formed in a 27% yield and a 64% yield, respectively, were identified by a combination of gas chromatographic-mass spectroscopy analyses, and were made up of the expected bis (3-cyclohexene) ketones and an unexpected mixture of dehydrogenated bis (3-cyclohexene) ketones. Therefore, the catalyst comprising $MnO_2$ on an alumina support not only functioned as a ketonic decarboxylative coupling catalyst, but also as a dehydrogenation catalyst.

EXAMPLE 13

A more complete dehydrogenation of a crude product mixture of the ketonic decarboxylative coupling of 3,4-dimethyl-3-cyclohexene carboxylic acid was accomplished by passing the crude product mixture over a 0.5 wt % platinum on alumina catalyst at a temperature of 385° C. This resulted in a 60 to 75% yield of 3,3',4,4'-tetramethylbenzophenone. The 3,4-dimethyl-3-cyclohexene carboxylic acid had been contacted with a 19 wt % $MnO_2/Al_2O_3$ catalyst at a temperature of about 360° C. and a pressure of about 15 psia for a contact time of about 7 sec.

The results presented hereinabove clearly demonstrate the production of benzophenones when contacting 3-cyclohexene carboxylic acids with catalysts comprising manganese dioxide.

What is claimed is:

1. A process for preparing a benzophenone from a 3-cyclohexene carboxylic acid, which process comprises contacting a feed containing a 3-cyclohexene carboxylic acid selected from the group consisting of 3-cyclohexene carboxylic acid, 4-methyl-3-cyclohexene carboxylic acid, 3,4-dimethyl-3-cyclohexene carboxylic acid and mixtures thereof in the vapor phase and at a temperature within the range of about 250° C. to about 500° C., a pressure within the range of about 5 psia to about 200 psia, and a contact time within the range of about 1 sec to 10 sec with a catalyst selected from the group consisting of $MnO_2$, $ThO_2$, $ZrO_2/Al_2O_3$ and $MnO_2/Al_2O_3$ to convert said carboxylic acid into a benzophenone.

2. The process of claim 1, wherein said catalyst comprises manganese dioxide on a support of catalytically active alumina, said manganese dioxide being present in an amount within the range of about 5 wt % to about 30 wt %, based upon the total weight of said catalyst.

3. The process of claim 2, wherein said catalytically active alumina has a surface area within the range of about 5 $m^2$/gm to about 400 $m^2$/gm.

4. The process of claim 1, wherein said $MnO_2$ is present in an amount within the range of about 10 wt % to about 25 wt %.

5. The process of claim 1, wherein said catalyst consists of 19 wt % $MnO^2$ upon a support of alumina.

* * * * *